(12) United States Patent
Tal

(10) Patent No.: US 6,994,693 B2
(45) Date of Patent: Feb. 7, 2006

(54) TUNNELER-NEEDLE COMBINATION FOR TUNNELED CATHETER PLACEMENT

(75) Inventor: Michael Tal, Woodbridge, CT (US)

(73) Assignee: Yale University, New Haven, CT (US)

( * ) Notice: Subject to any disclaimer, the term of this patent is extended or adjusted under 35 U.S.C. 154(b) by 227 days.

(21) Appl. No.: 10/197,746

(22) Filed: Jul. 17, 2002

(65) Prior Publication Data

US 2003/0088212 A1 May 8, 2003

Related U.S. Application Data

(60) Provisional application No. 60/306,063, filed on Jul. 17, 2001.

(51) Int. Cl.
*A61M 5/32* (2006.01)
*A61M 5/178* (2006.01)

(52) U.S. Cl. ................ 604/183; 604/158; 604/164.01; 604/164.05

(58) Field of Classification Search .......... 604/158, 604/164.01, 164.05, 164.06, 506, 49, 6.16, 604/510, 53, 170, 264, 272–274, 93.01, 160, 604/161, 164.07, 164.13, 166.01, 170.01; 606/108, 167, 190, 185
See application file for complete search history.

(56) References Cited

U.S. PATENT DOCUMENTS

| | | | |
|---|---|---|---|
| 3,633,579 A | * | 1/1972 | Alley et al. ................ 604/508 |
| 4,306,562 A | | 12/1981 | Osborne |
| 4,417,886 A | | 11/1983 | Frankhouser et al |
| 4,432,752 A | | 2/1984 | Marlon . |
| 4,453,928 A | | 6/1984 | Steiger |
| 4,629,450 A | | 12/1986 | Suzuki et al. |
| 4,911,691 A | * | 3/1990 | Aniuk et al. ............ 604/164.03 |
| 5,009,642 A | * | 4/1991 | Sahi ............................ 604/158 |
| 5,098,392 A | | 3/1992 | Fleischhacker et al. |
| 5,221,263 A | * | 6/1993 | Sinko et al. ................ 604/161 |
| 5,306,240 A | | 4/1994 | Berry |
| 5,380,290 A | | 1/1995 | Makower et al. |
| 5,792,110 A | * | 8/1998 | Cunningham ............... 604/158 |
| 5,919,160 A | | 7/1999 | Sanfilippo, II |
| 6,156,016 A | | 12/2000 | Maginot |
| 6,193,691 B1 | | 2/2001 | Beardsley |
| 6,206,871 B1 | | 3/2001 | Zanon et al. |
| 6,398,743 B1 | * | 6/2002 | Halseth et al. .............. 600/585 |
| 6,454,744 B1 | * | 9/2002 | Spohn et al. ........... 604/164.05 |
| 6,565,594 B1 | | 5/2003 | Herweck et al. |
| 6,613,069 B2 | | 9/2003 | Boyd et al. |
| 6,638,210 B2 | * | 10/2003 | Berger ......................... 600/30 |
| 6,641,564 B1 | * | 11/2003 | Kraus ....................... 604/164.1 |
| 2001/0032023 A1 | | 10/2001 | Herweck et al. |
| 2003/0125789 A1 | | 7/2003 | Ross et al. |

FOREIGN PATENT DOCUMENTS

GB  979919  1/1965

* cited by examiner

*Primary Examiner*—Nicholas D. Lucchesi
*Assistant Examiner*—Catherine S. Williams
(74) *Attorney, Agent, or Firm*—Welsh & Flaxman LLC

(57) ABSTRACT

An access system for providing subcutaneous access to a vessel, organ, or body cavity comprises a needle and a rigid or semi-rigid tunneler arranged coaxially around the needle, such that the needle moves slidably within the tunneler. Optionally a sheath may be positioned coaxial to the tunneler. The tunneler-needle system is inserted through an incision in a patient's skin to initiate a procedure whereby a catheter is inserted into the vessel, organ, or body cavity.

22 Claims, 5 Drawing Sheets

US 6,994,693 B2

TUNNELER-NEEDLE COMBINATION FOR TUNNELED CATHETER PLACEMENT

CROSS-REFERENCE TO RELATED APPLICATION

This application is based upon U.S. provisional patent application Ser. No. 60/306,063, filed Jul. 17, 2001, which is incorporated herein by reference in its entirely.

FIELD OF THE INVENTION

The invention relates to an improved method of subcutaneous catheter placement. More particularly, this invention relates to vascular and other body cavity access systems implanted in individuals for dialysis or medication.

BACKGROUND OF THE INVENTION

In the treatment of many illnesses, it is necessary to repeatedly infuse medication directly into the bloodstream, into a particular organ, or otherwise to a particular medication site. For example, various chemotherapy regimes for treatment of cancerous conditions require frequent periodic medication. Bowel diseases and bone infections are other examples of conditions which require repeated treatment, as does the periodic dispensing of pain medication for terminally ill patients. In such frequent medication situations, to avoid having to locate a blood vessel for injection by needle each time, it is preferred to implant a catheter into the circulatory system through which the medication can be infused. Likewise, catheters are implanted to dispense medication directly to diseased or other treatment sites. Often, the medication is toxic in concentrated amounts and, therefore, must be infused through a catheter into a large volume of blood. To accomplish this, the catheter is fed through a vessel to a large vein or a chamber of the heart. Catheters are also used for dispensing dialysis fluid to the peritoneal cavity for the purpose of peritoneal dialysis Various removable devices have been developed to administer medications to the large veins in the body or to a chamber in the heart, including external extending catheters, such as those referred to as BROVIAC, GROSHONG, and HICKMAN catheters. Another general type of system which is wholly implanted is generally referred to as a vascular port, such as, for example, PORT-A-CATH®, available from Pharmacia Deltec, Inc., St. Paul, Minn., or as disclosed in U.S. Pat. No. 5,281,205 to McPherson, or VITAL-PORT® available from Cook Inc. of Bloomington, Ind.

A problem that arises with some implanted vascular access systems is that, despite steps taken after they are used to keep them clean, the patient may become infected at the site where the catheter is inserted. Given sufficient time, any catheter system that leaves the access opening external of the body will necessarily develop infection at the site where the catheter passes through the skin. While fully implanting a catheter device may reduce the problem of infection, other devices which are fully implanted require more invasive surgery, resulting in more discomfort, greater expense, and a longer recovery period. Moreover, these invasive techniques tend to form unsightly scars and scar tissue.

Tunneled catheters help reduce the chance for infection. Externally extending catheters are typically implanted using a guidewire, which is inserted through a first, vena-puncture incision into a patient's body and directed to the point of application, e.g., a vein or an organ, through the lumen of a needle. Once the guidewire is in place in the vein or organ, a peelaway sheath is fitted on a dilator and guided distally over the guidewire by the dilator. When the dilator is withdrawn, the sheath forms a tunnel through the first incision to the point of application. A tunneler having the proximal end affixed to a catheter, such as a dialysis catheter, is inserted into a second incision about 5 to 10 cm from the first incision, and the distal end of the tunneler is worked subcutaneously to the first incision, where the tunneler and catheter distal end are pulled out of the first incision. Then, after the distal end of the catheter is disengaged from the tunneler proximal end, the catheter distal end is inserted into the sheath proximal end. The catheter is pushed through the sheath to the point of application, the sheath is peeled away, and the first incision is closed, so that the catheter extends from the second incision to the point of application.

The above-described procedure has a number of disadvantages. For example, air embolization is a major potential complication. Also, there is the trauma associated with making two incisions, which could result in additional scarring and/or infection. Further, there is a potential technical problem of "kinking" the catheter during insertion. In addition, this procedure is somewhat time-consuming, taking from about 30 to 60 minutes to complete.

Tunneled catheters are used for the purpose of dialysis. For hemodialysis a tunneled double lumen catheter is placed in the veins of the chest, usually the jugular or subclavian veins, with the tip of the catheter in the superior vena cava or the right atrium. For peritoneal dialysis a tunneled single lumen catheter is placed into the peritoneal cavity with the tip usually in the pelvis.

OBJECTS OF THE INVENTION

It is an object of the invention to provide an improved method and apparatus of subcutaneous catheter placement.

It is also an object of the invention to provide a vascular access system for implanting a catheter in an individual for hemodialysis or peritoneal dialysis.

It is a further object of the invention to provide a vascular or corporeal access system for medication.

It is yet a further object of the invention to provide a tunneler-needle system wherein tunneled vascular access can be achieved with a single incision.

These and other objects of the invention will become more apparent from the description below.

SUMMARY OF THE INVENTION

According to the invention, subcutaneous vascular access is provided using a tunneler-needle combination. The tunneler-needler combination comprises a needle and a tunneler arranged circumferentially around the needle. Optionally a sheath may be arranged circumferentially around the tunneler.

To subcutaneously implant a catheter according to the invention, an incision is made in the patient's skin at a point above or adjacent to a desired vessel, organ, or body cavity. Then, the tunneler-needle combination is inserted, blunt dissection, so that the distal tip of the needle is adjacent the vessel, organ, or body cavity. The needle is advanced so that the tip of the tunneler-needle punctures the vessel, organ, or body cavity. A guidewire is threaded through the needle lumen so that the distal end of the guidewire is in the vessel, organ, or body cavity, and then the needle and tunneler are withdrawn. A catheter can then be threaded over the guidewire to the vessel, organ, or body cavity. When the catheter distal tip is in the vessel, organ, or body cavity, the guidewire is withdrawn.

Optionally a sheath is arranged around the tunneler, which sheath remains in position when the needle and tunneler are withdrawn. Then the catheter is threaded over the guidewire through the sheath. Once the catheter is in position, the sheath is peeled away and is withdrawn.

DETAILED DESCRIPTION OF THE INVENTION

Figure 1:
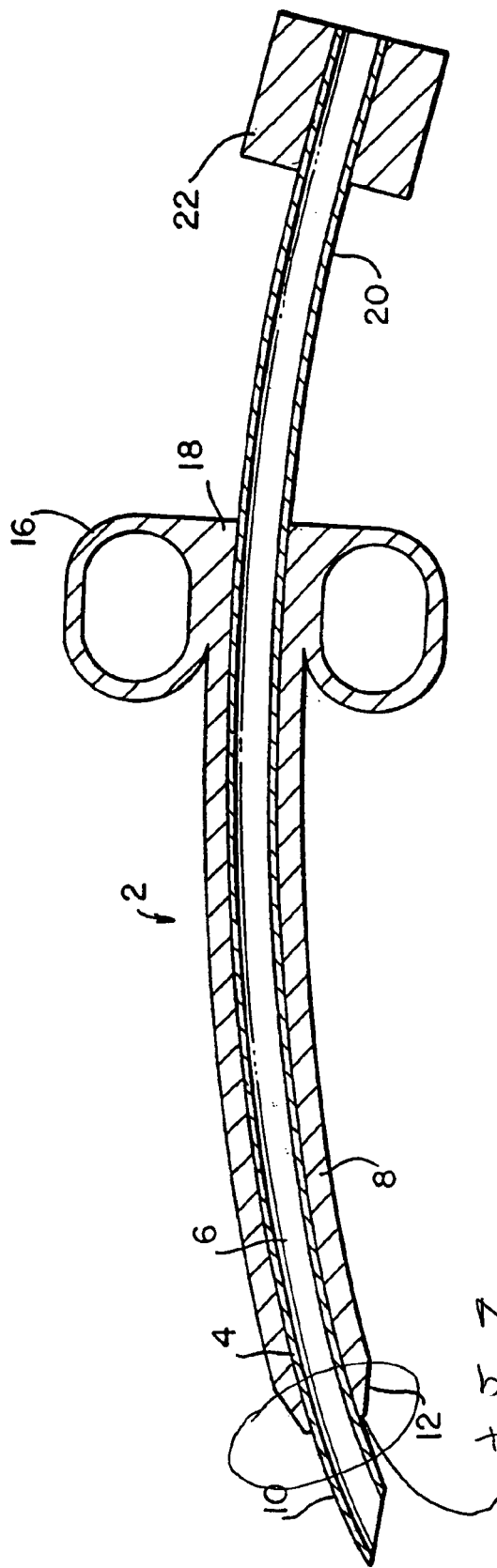
FIGS. 1 and 2 are each a cross-sectional view of a tunneler-needle system according to the invention.

The invention can perhaps be better understood from the drawings. In FIG. 1, a tunneler-needle system 2 compromises a needle 4 with a lumen 6 and a tunneler 8 arranged coaxially around needle 4. The distal end 10 of needle 4 preferably is obliquely angled and sharp, and the distal end 12 of tunneler 8 can be tapered, sharp, blunt, shaped like a needle, or any other useful shape.

Preferably tunneler 8 has grips 16 at its proximal end 18 to facilitate handling. Also, the proximal end 20 of needle 4 has a port/connector 22.

Figure 2:
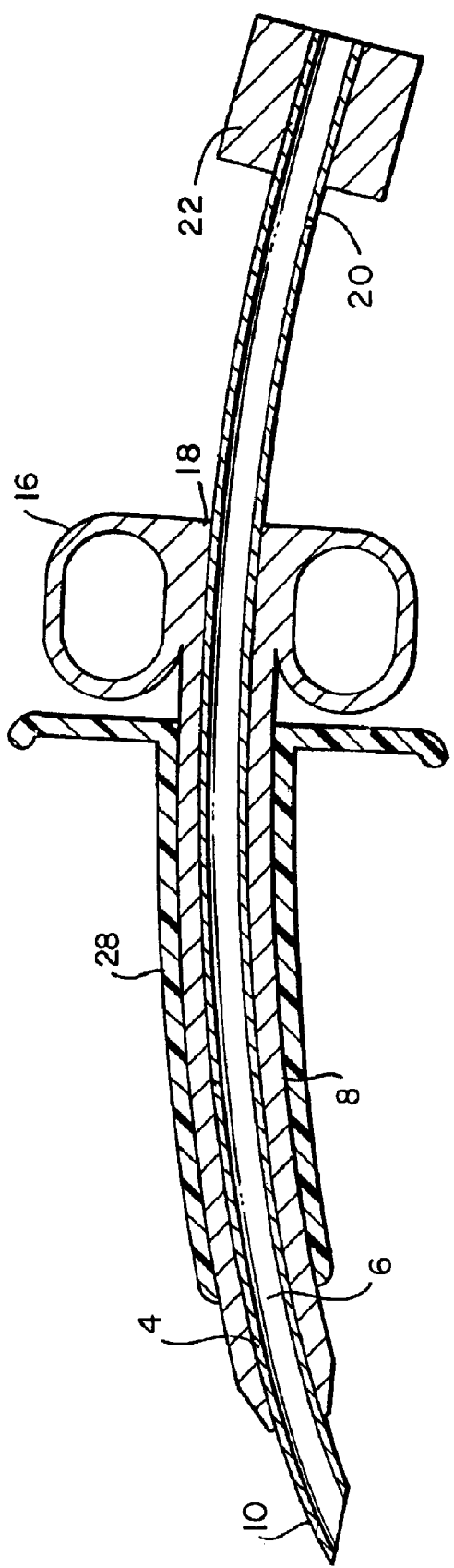

The embodiment of the invention set forth in FIG. 2 is similar to the embodiment of FIG. 1 with the addition of a sheath 28.

Needle 4 is a conventional vascular access device. On the otherhand, whereas a conventional vascular tunneler is solid, blunt, rigid, and/or slightly angled, tunneler 8 is a hollow tube of any sort and can be angled, straight, or slightly curved, including, but not limited to, being shaped like a needle. Preferably tunneler 8 is a physiologically acceptable metal or polymer such as stainless steel, titanium, polyethylene or polyurethane. Sheath 28 is preferably a conventional peelaway sheath made of a suitable polymer such as polytetrafluroethylene, polyethylene, or polyurethane.

Figure 3:
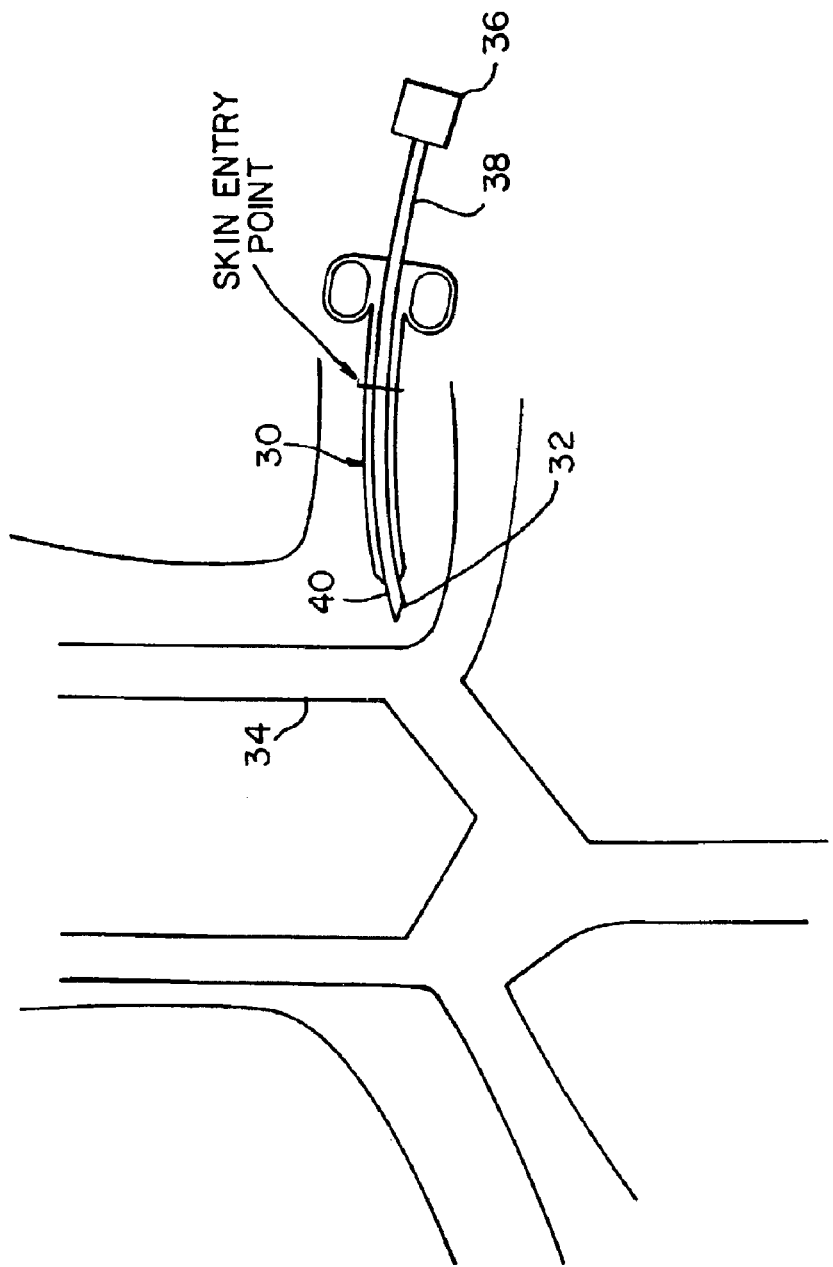
FIGS. 3 and 4 are each a schematic representation of the positioning of a tunneler-needle system within a patient's body.
Figure 4:
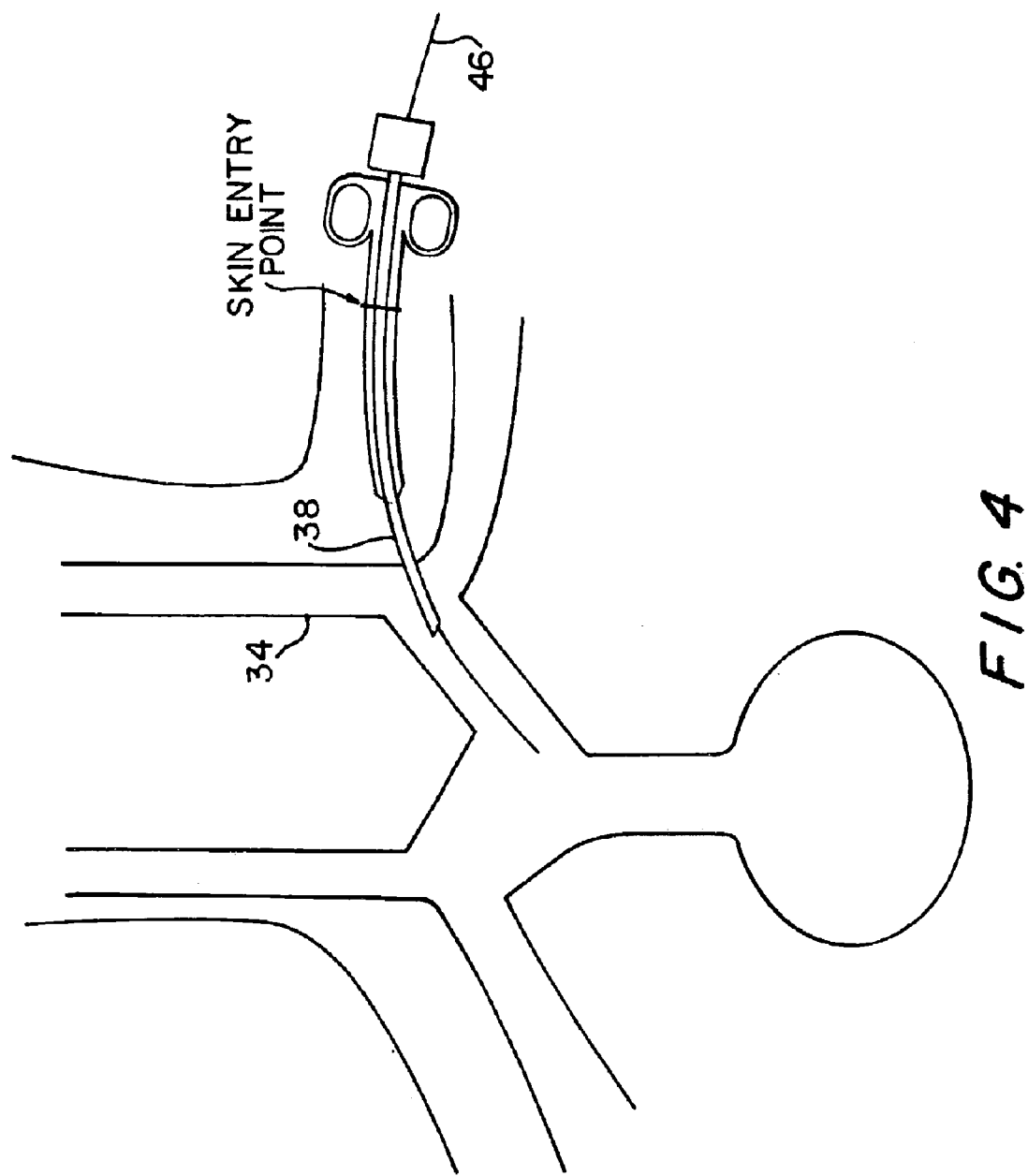

FIG. 3 depicts a tunneler-needle system 30 where the system distal end 32 is adjacent a vessel such as jugular vein 34. With ultrasonic guidance the proximal end 36 of needle 38 is advanced so that needle distal end 40 punctures vein 34. Then, as shown in FIG. 4, a guidewire 46 is advanced through needle 38 into vein 34. Tunneler-needle system 30 is withdrawn, and then a catheter (not shown) is advanced distally over guidewire 46.

Figure 5:
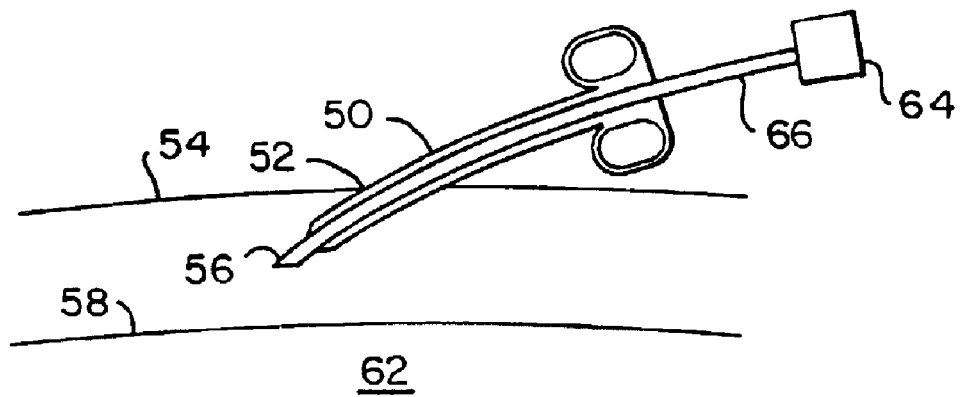
FIGS. 5 and 6 are each a schematic representation of the positioning of a tunneler-needle system in the abdominal wall for gaining access to the peritoneal cavity.
Figure 6:
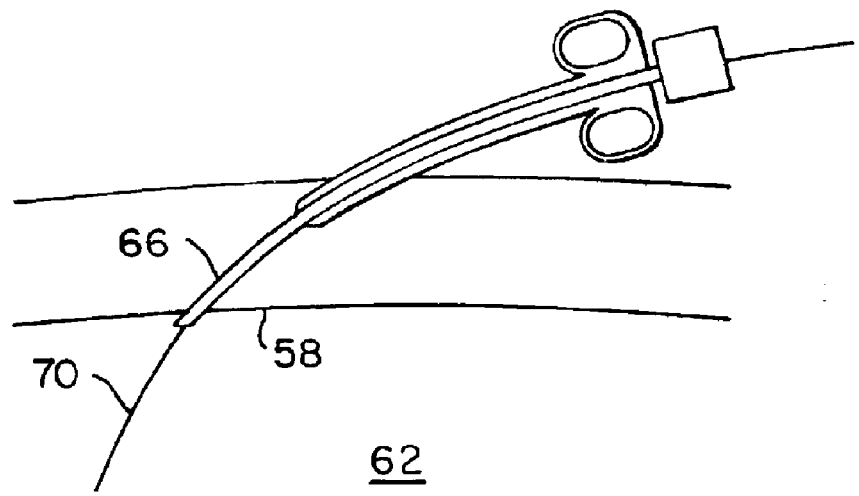

As shown in FIG. 5, a tunneler-needle system 50 can be inserted through an incision 52 in a patient's abdominal wall 54. The system distal end 56 is adjacent the peritoneum 58, which defines the peritoneal cavity 62. The proximal end 64 of needle 66 is advanced, with or without ultrasound guidance, so that needle distal tip 68 punctures the patient's peritoneum 58. Then, as shown in FIG. 6, a guidewire 70 is advanced through needle 66 into peritoneal cavity 62.

Preferably the catheter will have a tapered, slightly stiff distal end and a conventional hydrophilic coating. Optionally tunneler-needle 30 may have a coaxially arranged sheath, which may have a hydrophilic coating. The sheath would remain in place after the needle and tunneler are removed, and the catheter would be threaded through the sheath. Once the catheter is inserted into the desired vein or organ, the sheath would be removed, preferably by peeling it away.

Among the several advantages of the invention is that the procedure should only take about 10 to 15 minutes.

It will be further apparent to one skilled in this art that the improvements provided for in the present invention, while described with relation to certain specific physical embodiments also lend themselves to being applied in other physical arrangements not specifically provided for herein, which are nonetheless within the spirit and scope of the invention taught here.

I claim:

1. An access system for providing access to a vessel, organ or body cavity through a subcutaneous tunnel, which comprises:
   a) a needle having a distal end and a proximal end, and
   b) a rigid or semi-rigid tunneler arranged coaxially around the needle and having a distal end and a proximal end, the distal end having a blunt shape for dissection of a subcutaneous tunnel, the distal end of the tunneler further having an opening to facilitate passing of the needle and the needle exits the opening at an oblique angle with respect to a plane in which the opening lies, and
   c) a guidewire shaped and dimensioned for passage through the needle,
   wherein the needle moves slidably within the tunneler, the needle proximal end has a gripping member for advancing the needle, which needle proximal end has a port for receiving the guidewire, and the tunneler proximal end has a gripping member.

2. The system of claim 1, wherein the tunneler is a hollow tube.

3. The system of claim 1, wherein the tunneler is straight, angled or slightly curved.

4. The system of claim 1, wherein the tunneler is comprised of a physiologically acceptable metal or polymer.

5. The system of claim 4, wherein the tunneler comprises stainless steel.

6. An access system for providing access to a vessel organ, or body cavity through a subcutaneous tunnel, which comprises:
   a) a needle having a distal end and a proximal end,
   b) a rigid or semi-rigid tunneler arranged coaxially around the needle and having a distal end and a proximal end, wherein the distal end of the tunneler is blunt to facilitate blunt dissection of a subcutaneous tunnel, and
   c) a sheath arranged coaxially around the tunneler,
   wherein the needle moves slidably within the tunneler and the needle proximal end has a port and a gripping member for advancing the needle, and wherein the port receives a guidewire.

7. The system of claim 6, wherein the tunneler is straight, angled, or slightly curved.

8. The system of claim 6, wherein the distal end of the tunneler has an opening to facilitate passage of the needle.

9. The system of claim 6, wherein the tunneler is comprised of a physiologically acceptable metal or polymer.

10. The system of claim 9, wherein the tunneler comprises stainless steel.

11. The system of claim 6, wherein the proximal end of the tunneler has a gripping member.

12. The system of claim 6, wherein the sheath is a peelaway sheath, catheter or tubular structure.

13. The system of claim 6, wherein the distal end of the tunneler has an opening to facilitate passing of the needle and the needle exits the opening at an oblique angle with respect to a plane in which the opening lies.

14. An access system for providing access to a vessel organ, or body cavity through a subcutaneous tunnel, which comprises:
   a) a needle having a distal end and a proximal end,
   b) a rigid or semi-rigid tunneler arranged coaxially around the needle and having a distal end and a proximal end, wherein the distal end of the tunneler is blunt to facilitate blunt dissection of a subcutaneous tunnel, and
   c) a sheath arranged coaxially around the tunneler,
   wherein the needle moves slidably within the tunneler and the needle proximal end has a port and a gripping member for advancing the needle, and wherein the sheath is a peelaway sheath.

15. A method for providing subcutaneous access to a vessel, organ, or body cavity, which comprises the steps of:
   a) creating an incision in the skin of a patient a substantial distance from a vessel, organ, or body cavity;
   b) inserting an access system which comprises:
      i. a needle having a distal end and a proximal end, and
      ii. a rigid or semi-rigid tunneler arranged coaxially around the needle and having
   a distal end and a proximal end, the distal end having a blunt shape for dissection of a subcutaneous tunnel, wherein the needle moves slidably within the tunneler, the needle proximal end has a gripping member for advancing said needle, which needle proximal end has a port for receiving a guidewire, and the tunneler proximal end his a gripping member, the gripping member is for advancing through the incision and advancing the access system under the skin to create a subcutaneous tunnel to cause the distal end of the tunneler to be adjacent to the vessel, organ, or body cavity;
   c) advancing the distal end of the needle through the tunneler into the vessel, organ or body cavity;
   d) advancing a guidewire through the needle into the vessel, organ, or body cavity;
   e) withdrawing the tunneler and needle;
   f) advancing a flexible catheter through the subcutaneous tunnel over the guidewire into the vessel, organ, or body cavity; and
   g) withdrawing the guidewire.

16. A method for providing subcutaneous access to a vessel, organ, or body cavity, which comprises the steps of:
   a) creating an incision in the skin of a patient a substantial distance from a vessel, organ, or body cavity;
   b) inserting an access system which comprises:
      i. a needle having a distal end and a proximal end,
      ii. a rigid or semi-rigid tunneler arranged coaxially around the needle and having
   a distal end and a proximal end,
      iii. a sheath arranged coaxially around the tunneler, wherein the needle moves slidably within the tunneler, the needle proximal end has a port and a gripping member for advancing said needle,
   through the incision and advancing the access system under the skin to create a subcutaneous tunnel to cause the distal end of the tunneler to be adjacent to the vessel, organ, or body cavity;
   c) advancing the distal end of the needle through the tunneler into the vessel, organ or body cavity;
   d) advancing a guidewire through the needle into the vessel, organ, or body cavity;
   e) withdrawing the tunneler and needle;
   f) advancing a flexible catheter through the subcutaneous tunnel over the guidewire and through the sheath into the vessel, organ, or body cavity;
   g) withdrawing the guidewire; and
   h) peeling the sheath away.

17. An access system for providing access to a vessel, organ, or body cavity through a subcutaneous tunnel, which comprises:
   a) a needle having a distal end and a proximal end,
   b) a rigid or semi-rigid tunneler arranged coaxially around the needle and having a distal end and a proximal end, wherein the distal end of the tunneler is blunt to facilitate blunt dissection of a subcutaneous tunnel, and
   c) a sheath arranged coaxially around the tunneler,
   wherein the needle moves slidably within the tunneler and the needle proximal end has a port and a gripping member for advancing the needle, and, wherein the tunneler is curved.

18. An access system for providing subcutaneous access to a vessel, organ, or body cavity, which comprises:
   a) a substantially rigid tunneler having a distal end and a proximal end and having a lumen therethrough, the tunneler being curved and the distal end having a blunt shape for dissection of a subcutaneous tunnel,
   b) a needle positioned within the lumen, the needle having a distal end and a proximal end; and
   c) a sheath arranged coaxially around the tunneler,
   wherein the needle moves slidably within the tunneler, the needle proximal end has a gripping member for advancing the needle, which needle proximal end has a port for receiving a guidewire, and the tunneler proximal end has a gripping member.

19. A method for providing subcutaneous access to a vessel, organ, or body cavity, which comprises the steps of:
   a) creating an incision in the skin of a patient a substantial distance from a vessel, organ, or body cavity;
   b) inserting an access system which comprises:
   a rigid or semi-rigid tunneler having a distal end and a proximal end and having a lumen therethrough,
      ii. a needle positioned within said lumen, said needle having a distal end and a proximal end, and
      iii. a sheath arranged coaxially around the tunneler,
   wherein the needle moves slidably within the tunneler, the needle proximal end has a gripping member for advancing said needle, which needle proximal end has a port for receiving a guidewire, and the tunneler proximal end has a gripping member, through the incision and advancing the access system under the skin to create a subcutaneous tunnel to cause the distal end of the tunneler to be adjacent to the vessel, organ, or body cavity;
   c) advancing the distal end of the needle through the tunneler into the vessel, organ or body cavity;
   d) advancing a guidewire through the needle into the vessel, organ, or body cavity;
   e) withdrawing the tunneler and needle;
   f) advancing a flexible catheter through the subcutaneous tunnel over the guidewire and through the vessel, organ, or body cavity;
   g) withdrawing the guidewire; and
   h) peeling the sheath away.

20. An access system for providing access to a vessel, organ or body cavity through a subcutaneous tunnel, which comprises:
   a) a needle having a distal end and a proximal end, and
   b) a substantially rigid tunneler arranged coaxially around the needle and having a distal end and a proximal end, the tunneler being curved and the distal end having a blunt shape for dissection of a subcutaneous tunnel, and
   c) a guidewire shaped and dimensioned for passage through the needle,
   wherein the needle moves slidably within the tunneler, the needle proximal end has a gripping member for advancing the needle, which needle proximal end has a port for receiving a guidewire, and the tunneler proximal end has a gripping member.

21. An access system for providing access to a vessel, organ or body cavity through a subcutaneous tunnel, which comprises:
   a) a needle having a distal end and a proximal end, and
   b) a rigid or semi-rigid tunneler arranged coaxially around the needle and having a distal end and a proximal end, the distal end of the tunneler having an opening to facilitate passing of the needle and the needle exits the opening at an oblique angle with respect to a plane in which the opening lies, and
   c) a guidewire shaped and dimensioned for passage through the needle,
   wherein the needle moves slidably within the tunneler, the needle proximal end has a gripping member for advancing the needle, which needle proximal end has a port for receiving a guidewire, and the tunneler proximal end has a gripping member.

22. An access system for providing access to a vessel, organ, or body cavity through a subcutaneous tunnel, which comprises:
   a) a needle having a distal end and a proximal end,
   b) a rigid or semi-rigid tunneler arranged coaxially around the needle and having a distal end and a proximal end, the distal end of the tunneler includes an opening to facilitate passage of the needle and the needle exits the opening at an oblique angle with respect to a plane in which the opening lies, and
   c) a sheath arranged coaxially around the tunneler,
   wherein the needle moves slidably within the tunneler and the needle proximal end has a port and a gripping member for advancing the needle.

* * * * *